United States Patent
Chopra et al.

(10) Patent No.: US 10,696,857 B2
(45) Date of Patent: Jun. 30, 2020

(54) CURABLE GELLANT INK

(71) Applicant: Xerox Corporation, Norwalk, CT (US)

(72) Inventors: Naveen Chopra, Oakville (CA); Michelle N. Chrétien, Mississauga (CA); Jennifer L. Belelie, Oakville (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 15/842,525

(22) Filed: Dec. 14, 2017

(65) Prior Publication Data
US 2019/0185694 A1 Jun. 20, 2019

(51) Int. Cl.
| | | |
|---|---|---|
| C09D 11/34 | (2014.01) | |
| C09D 11/38 | (2014.01) | |
| C09D 11/101 | (2014.01) | |
| C09D 11/00 | (2014.01) | |
| C09D 11/30 | (2014.01) | |
| B41J 2/01 | (2006.01) | |
| B41M 5/00 | (2006.01) | |
| B41M 7/00 | (2006.01) | |
| C07C 235/78 | (2006.01) | |
| C07C 275/26 | (2006.01) | |

(52) U.S. Cl.
CPC .......... *C09D 11/38* (2013.01); *B41J 2/01* (2013.01); *B41M 5/0023* (2013.01); *B41M 7/0081* (2013.01); *C07C 235/78* (2013.01); *C07C 275/26* (2013.01); *C09D 11/00* (2013.01); *C09D 11/101* (2013.01); *C09D 11/30* (2013.01); *C09D 11/34* (2013.01); *B41J 2002/012* (2013.01); *C07C 2601/14* (2017.05)

(58) Field of Classification Search
CPC ....... C09D 11/38; C09D 11/101; C09D 11/34; C07C 235/78; C07C 275/26; C07C 2601/14; B41M 5/0023; B41M 7/0081; B41J 2/01; B41J 2002/012; B41J 2/0057
See application file for complete search history.

(56) References Cited

U.S. PATENT DOCUMENTS

| | | | |
|---|---|---|---|
| 4,659,383 A * | 4/1987 | Lin ................. | C09D 11/34 106/31.29 |
| 4,889,560 A | 12/1989 | Jaeger et al. | |
| 4,889,761 A | 12/1989 | Titterington et al. | |
| 5,041,161 A * | 8/1991 | Cooke ............... | C09D 11/34 106/31.29 |
| 5,194,638 A | 3/1993 | Frihart et al. | |
| 5,221,335 A | 6/1993 | Williams et al. | |
| 5,372,852 A | 12/1994 | Titterington et al. | |
| 5,389,958 A | 2/1995 | Bui et al. | |
| 5,621,022 A | 4/1997 | Jaeger et al. | |
| 5,783,657 A | 7/1998 | Pavlin et al. | |
| 5,998,570 A | 12/1999 | Pavlin et al. | |
| 6,111,055 A | 8/2000 | Berger et al. | |
| 6,350,889 B1 | 2/2002 | Pavlin | |
| 6,399,713 B1 | 6/2002 | MacQueen et al. | |
| 6,492,458 B1 | 12/2002 | Pavlin | |
| 6,787,658 B2 | 9/2004 | Cyr et al. | |
| 6,870,062 B2 | 3/2005 | Cyr et al. | |
| 6,870,063 B2 | 3/2005 | Cyr et al. | |
| 7,141,685 B2 | 11/2006 | Cyr et al. | |
| 7,259,275 B2 | 5/2007 | Belelie et al. | |
| 7,271,284 B2 | 5/2007 | Toma et al. | |
| 7,276,614 B2 | 5/2007 | Toma et al. | |
| 7,279,587 B2 | 5/2007 | Odell et al. | |
| 7,293,868 B2 | 11/2007 | Odell et al. | |
| 7,317,122 B2 | 1/2008 | Carlini et al. | |
| 7,449,515 B2 | 11/2008 | Belelie et al. | |
| 7,501,015 B2 | 3/2009 | Odell et al. | |
| 7,538,145 B2 | 5/2009 | Belelie et al. | |
| 7,541,406 B2 | 6/2009 | Banning et al. | |
| 7,559,639 B2 | 7/2009 | Belelie et al. | |
| 7,563,313 B2 | 7/2009 | Goredema et al. | |
| 7,563,314 B2 | 7/2009 | Breton et al. | |
| 7,563,489 B2 | 7/2009 | Carlini et al. | |
| 7,572,325 B2 | 8/2009 | Breton et al. | |
| 7,578,587 B2 | 8/2009 | Belelie et al. | |
| 7,578,875 B2 | 8/2009 | Breton et al. | |
| 7,625,956 B2 | 12/2009 | Odell et al. | |
| 7,632,546 B2 | 12/2009 | Odell et al. | |
| 7,665,835 B2 | 2/2010 | Goredema et al. | |
| 8,084,637 B2 | 12/2011 | Chopra et al. | |
| 8,097,661 B2 | 1/2012 | Chopra et al. | |
| 8,507,584 B2 | 8/2013 | Chopra et al. | |
| 8,603,612 B2 | 12/2013 | Chopra et al. | |
| 8,882,256 B2 | 11/2014 | Chopra et al. | |
| 8,940,935 B2 | 1/2015 | Chopra et al. | |
| 9,328,248 B2 | 5/2016 | Chopra et al. | |
| 2006/0204768 A1 * | 9/2006 | King .................. | B41J 2/0057 428/447 |
| 2011/0263769 A1 | 10/2011 | Chopra et al. | |
| 2014/0213684 A1 | 7/2014 | Chopra et al. | |
| 2018/0105712 A1 * | 4/2018 | Birau ................. | C09D 11/101 |

FOREIGN PATENT DOCUMENTS

EP          3498786    *    6/2019     ............ C09D 11/00

OTHER PUBLICATIONS

Extended European Search Report issued in European Application No. 18212112.9-1102, dated May 6, 2019.
Canadian Office Action issued in Canadian Application No. 3,027,063, dated Dec. 19, 2019.

* cited by examiner

*Primary Examiner* — Huan H Tran
(74) *Attorney, Agent, or Firm* — Marylou J. Lavoie, Esq. LLC

(57) ABSTRACT

An ink composition including at least one curable monomer; at least one gellant; an optional photoinitiator; and an optional colorant; wherein the ink composition has a viscosity of less than $10^6$ centipoise at a temperature of from about 20° C. to about 40° C.; and wherein the ink composition has the characteristics of being both ink jettable and pinnable at a temperature of from about 20° C. to about 40° C.

18 Claims, 2 Drawing Sheets

CURABLE GELLANT INK

BACKGROUND

Disclosed herein is an ink composition comprising at least one curable monomer; at least one gellant; an optional photoinitiator; and an optional colorant; wherein the ink composition has a viscosity of less than $10^6$ centipoise at a temperature of from about 20° C. to about 40° C.; and wherein the ink composition has the characteristics of being both ink jettable and pinnable at a temperature of from about 20° C. to about 40° C.

Also disclosed is a method for printing comprising disposing an ink composition in an imagewise pattern onto an intermediate transfer member or directly onto a final image receiving substrate; optionally, when an intermediate transfer member is used, transferring the ink in the imagewise pattern from the intermediate transfer member to a final recording substrate; exposing the imagewise pattern to radiation to cure the ink; wherein the ink composition comprises at least one curable monomer; at least one gellant; an optional photoinitiator; and an optional colorant; wherein the ink composition has a viscosity of less than $10^6$ centipoise at a temperature of from about 20° C. to about 40° C.; and wherein the ink composition has the characteristics of being both ink jettable and pinnable at a temperature of from about 20° C. to about 40° C.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing.

Phase change inks for color printing typically comprise a phase change ink carrier composition which is combined with a phase change ink compatible colorant. A series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. Nos. 4,889,560, 4,889,761, and 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes. The colorants can also include pigments, as disclosed in, for example, U.S. Pat. No. 5,221,335, the disclosure of which is totally incorporated herein by reference. U.S. Pat. No. 5,621,022, the disclosure of which is totally incorporated herein by reference, discloses the use of a specific class of polymeric dyes in phase change ink compositions.

Phase change inks have also been used for applications such as postal marking, industrial marking, and labeling.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Suitable carrier materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers.

Current ultraviolet curable gellant inks are liquid at elevated temperatures, typically having viscosities of from about 10 to about 15 centipoise at jetting temperatures, with jetting temperatures typically being from about 80° C. about 120° C., and having a viscosity of greater than $10^4$ centipoise at room temperature (about 25° C.) which pins the ink drops in place, sometimes without the need for intermediate cure. After printing, the printed markings are cured to provide robust images.

U.S. Pat. No. 7,501,015, which is hereby incorporated by reference herein in its entirety, describes in the Abstract thereof a phase change ink that has a viscosity of from about 4 mPa-s to about 50 mPa-s at a first temperature and has a viscosity of from $10^4$ mPa-s to about $10^9$ mPa-s at a second lower temperature. The second temperature may be below the first temperature by at least 10° C., but by no more than 50° C. The first temperature may be from about 60° C. to about 110° C. and the second temperature may be from about 20° C. to about 70° C. A curve of $\log_{10}$ viscosity of the phase change ink plotted against temperature in degrees Celsius may have a slope having an absolute value less than 0.02 at the first temperature and have a slope having an absolute value greater than 0.08 for at least a region second temperature.

U.S. Pat. No. 8,507,584, which is hereby incorporated by reference herein in its entirety, describes in the Abstract thereof a phase change ink comprising a colorant, an initiator, and a phase change ink carrier, said carrier comprising at least one radically curable monomer compound and a compound of the formula

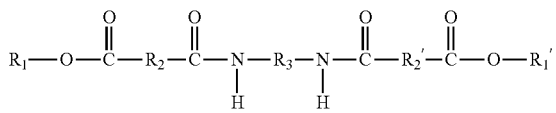

wherein $R_1$ and $R_{1'}$ are the same, and wherein $R_1$ and $R_{1'}$ are each an aromatic group; and wherein $R_2$ and $R_{2'}$ and $R_3$ each, independently of the others, are alkylene groups, arylene groups, arylalkylene groups, or alkylarylene groups; or wherein, in embodiments, $R_1$ and $R_{1'}$ can be the same or different, and wherein $R_1$ and $R_{1'}$ each, independently of the other is an alkyl group having at least one ethylenic unsaturation, an arylalkyl group having at least one ethylenic unsaturation, an alkylaryl group having at least one ethylenic unsaturation, or an aromatic group, provided that at least one of $R_1$ and $R_{1'}$ is an aromatic group; and provided that neither of $R_1$ or $R_1{}'$ is a photoinitiator group. Also disclosed herein is a method of printing with the phase change ink.

U.S. Pat. No. 8,882,256, which is hereby incorporated by reference herein in its entirety, describes in the Abstract thereof curable solid inks which are solid at room temperature and molten at an elevated temperature at which the molten ink is applied to a substrate. In particular, the curable solid inks comprise low molecular weight amide gellants that impart self-leveling capabilities to the inks. Also disclosed herein are methods for making the amide gellant and the inks comprising the amide gellants.

U.S. Pat. No. 8,940,935, which is hereby incorporated by reference herein in its entirety, describes in the Abstract thereof curable inks including a bis-urea gelator having the structure of Formula I

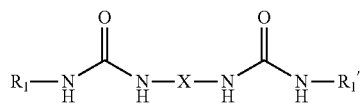

wherein R and R' each, independently of the other, is a saturated aliphatic hydrocarbon group selected from the group consisting of (1) linear aliphatic groups, (2) branched aliphatic groups, (3) cyclic aliphatic groups, (4) aliphatic groups containing both cyclic and acyclic portions, any carbon atom of the saturated aliphatic hydrocarbon groups may be optionally substituted with an alkyl group (cyclic or acyclic), wherein (1) and (2) groups have a carbon number of from about 1 to about 22 carbons, and wherein (3) and (4) groups have a carbon number of from about 4 to about 10 carbons; and X is selected from the groups consisting of: (i) an alkylene groups, (ii) an arylene group, (iii) an arylalkylene group, and (iv) an alkylarylene group.

While known compositions and processes may be suitable for their intended purposes, a need remains for improved phase change ink compositions. Further, a need remains for improved curable gellant ink compositions. Still further, a need remains for improved curable gellant ink compositions that can be jetted at reduced temperatures. Still further, a need remains for improved curable gellant ink compositions that retain the broad substrate latitude afforded by current compositions. Still further, a need remains for improved curable gellant ink compositions that can be jetted at reduced temperatures without the need for immediate curing after printing or jetting. Still further, a need remains for improved curable gellant ink compositions that are easy to spread or level.

The appropriate components and process aspects of the each of the foregoing U.S. Patents and Patent Publications may be selected for the present disclosure in embodiments thereof. Further, throughout this application, various publications, patents, and published patent applications are referred to by an identifying citation. The disclosures of the publications, patents, and published patent applications referenced in this application are hereby incorporated by reference into the present disclosure to more fully describe the state of the art to which this invention pertains.

SUMMARY

Described is an ink composition comprising at least one curable monomer; at least one gellant; an optional photoinitiator; and an optional colorant; wherein the ink composition has a viscosity of less than $10^6$ centipoise at a temperature of from about 20° C. to about 40° C.; and wherein the ink composition has the characteristics of being both ink jettable and pinnable at a temperature of from about 20° C. to about 40° C.

Also described is a method for printing comprising disposing an ink composition in an imagewise pattern onto an intermediate transfer member or directly onto a final image receiving substrate; optionally, when an intermediate transfer member is used, transferring the ink in the imagewise pattern from the intermediate transfer member to a final recording substrate; exposing the imagewise pattern to radiation to cure the ink; wherein the ink composition comprises at least one curable monomer; at least one gellant; an optional photoinitiator; and an optional colorant; wherein the ink composition has a viscosity of less than $10^6$ centipoise at a temperature of from about 20° C. to about 40° C.; and wherein the ink composition has the characteristics of being both ink jettable and pinnable at a temperature of from about 20° C. to about 40° C.

DETAILED DESCRIPTION

Figure 1:
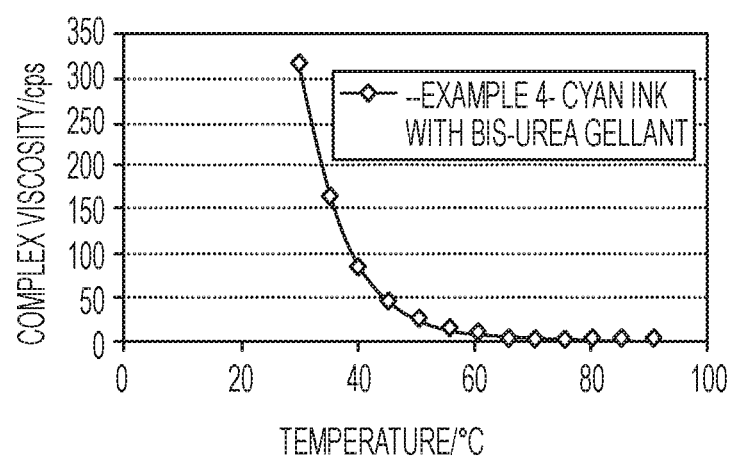
FIG. 1 is a graph showing complex viscosity (y-axis, centipoise) versus temperature (x-axis, ° C.) for an ink in accordance with the present disclosure.

Curable gellant ink compositions are provided having lower room temperature viscosities than prior such compositions, in embodiments, having room temperature viscosities of from about $10^2$ to about $10^4$ centipoise. The ink compositions retain the broad substrate latitude of previous such compositions and do not require immediate curing after printing. When the ambient substrate temperature is dropped, such as to 40° C., the ink compositions herein, having room temperature viscosities of from about $10^2$ to about $10^4$ centipoise, are still pinned in place, retaining the substrate latitude exhibited by higher viscosity designs, which is an unexpected and advantageous feature.

The ink compositions herein can comprise radiation curable monomers and/or oligomers, a photoinitiator, and a gelator or gellant. While currently known curable gellant ink compositions are liquid at elevated temperatures, such as having a viscosity of from about 10 to about 15 centipoise at jetting temperatures, typically of from about 80° C. to about 120° C., and have viscosities of greater than $10^4$ centipoise at room ambient temperature (substrate temperature), typically about 25° C., the present ink compositions provide lower room temperature viscosities, in embodiments, less than $10^6$ centipoise at a temperature of from about 20° C. to about 40° C. The ink compositions can be both disposed, such as ink jetted, and pinned at room temperature or a slightly elevated temperature above room temperature.

In embodiments, the gellant and gellant concentration in the ink composition is selected to impart to the ink composition the characteristic of being both ink jettable and pinnable at a temperature of from about 20° C. to about 40° C. By careful selection of one or more of gellant, gellant functional groups, gellant molecular weight, and concentration of gellant in the ink composition, a lower room temperature viscosity is achieved which enables both jetting and pinning at room temperature or a temperature slightly above room temperature, such as, from about 20° C. to about 40° C., or from about 20° C. to about 35° C., or from about 25° C. to about 35° C. In embodiments, an ink composition is provided comprising at least one curable monomer; at least one gellant; an optional photoinitiator; and an optional colorant; wherein the ink composition has a viscosity of less than $10^6$ centipoise at a temperature of from about 20° C. to about 40° C.; and wherein the ink composition has the characteristic of being both ink jettable and pinnable at a temperature of from about 20° C. to about 40° C.

As used herein, ink jettable means that the ink can be passed through a piezoelectric print head nozzle.

As used herein, pinnable means that the ink droplets that are jetted onto the substrate do not grow more than 20% of their original diameter (this is referred to as 'dot gain').

In embodiments, the ink composition has a viscosity of less than $10^6$ centipoise at a temperature of from about 20° C. to about 40° C. In embodiments, the ink composition has a viscosity of less than $10^5$ centipoise at a temperature of from about 20° C. to about 40° C. In other embodiments, the ink composition has a viscosity of from about $10^2$ centipoise to about $10^4$ centipoise at a temperature of from about 20° C. to about 40° C. In certain embodiments, the ink composition has a viscosity of from about $10^2$ centipoise to about $10^4$ centipoise at a temperature of from about 25° C. to about 35° C. In certain other embodiments, the ink composition has a viscosity of from about $10^{2.5}$ centipoise to about $10^{3.5}$ centipoise at a temperature of from about 20° C. to about 40° C. In certain other embodiments, the ink composition has a viscosity of from about $10^{2.5}$ centipoise to about $10^{3.5}$ centipoise at a temperature of from about 25° C. to about 35° C.

Any suitable or desired gellant or gelator can be selected provided that the gellant or combination of gellants imparts to the composition the desired functionality of being able to be jetted and pinned at the desired temperature as described herein. In embodiments, the at least one gellant is a gellant selected from the group consisting of amide gellants, bis-urea gellants, and combinations thereof.

In embodiments, the gellant can be selected from those described in U.S. Pat. No. 8,084,637, which is hereby incorporated by reference herein in its entirety. In embodiments, the gellant is a compound of the formula

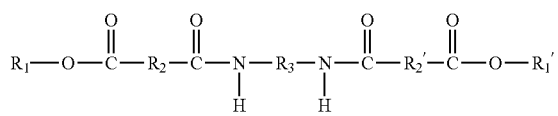

wherein $R_1$ and $R_{1'}$ can be the same or different, and wherein $R_1$ and $R_{1'}$ each, independently of the other is (i) an alkyl group having a least one ethylenic unsaturation therein, which can be linear or branched, cyclic or acyclic, and substituted or unsubstituted alkyl groups, and wherein hetero atoms may optionally be present in the alkyl group, (ii) an arylalkyl group having at least one ethylenic unsaturation therein, which can be substituted or unsubstituted arylalkyl groups, wherein the alkyl portion of arylalkyl group can be linear or branched, cyclic or acyclic, and substituted or unsubstituted, and wherein hetero atoms may optionally be present in either the aryl portion or the alkyl portion of the arylalkyl group, (iii) an alkylaryl group having at least one ethylenic unsaturation therein, which can be substituted or unsubstituted alkylaryl groups, wherein the alkyl portion of the alkylaryl group can be linear or branched, cyclic or acyclic, and substituted or unsubstituted, and wherein hetero atoms may optionally be present in either the aryl or the alkyl portion of the alkylaryl group, or (iv) an aromatic group, provided that at least one of $R_1$ and $R_{1'}$ is an aromatic group; and provided that neither of $R_1$ or $R_{1'}$ is a photoinitiator group;

wherein $R_2$ and $R_{2'}$ are the same or different, and wherein $R_2$ and $R_{2'}$ are each independently selected from (i) alkylene groups, which can be linear or branched, saturated or unsaturated, cyclic or acyclic, substituted or unsubstituted alkylene groups, and wherein hetero atoms may optionally be present in the alkylene group; (ii) arylene groups, which can be substituted or unsubstituted arylene groups, and wherein hetero atoms may optionally be present in the arylene group; (iii) arylalkylene groups, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) alkylarylene groups, which can be substituted or unsubstituted alkylarylene groups, wherein the alkyl portion of the alkylarylene group can be linear or branched, saturated or unsaturated, cyclic or acyclic, and substituted or unsubstituted, and wherein hetero atoms may optionally be present in either the aryl portion or the alkyl portion of the alkylarylene group; and wherein $R_3$ is (i) a linear or branched alkylene group, which can be saturated or unsaturated, and substituted or unsubstituted alkylene groups, and wherein hetero atoms may optionally be present in the alkylene group; (ii) an arylene group, which can be substituted or unsubstituted arylene groups, and wherein hetero atoms may optionally be present in the arylene group; (iii) an arylalkylene group, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) an alkylarylene group, which can be substituted or unsubstituted alkylarylene groups, wherein the alkyl portion of the alkylarylene group can be linear or branched, saturated or unsaturated, cyclic or acyclic, and substituted or unsubstituted, and where hetero atoms may optionally be present in either the aryl portion or the alkyl portion of the alkylarylene group.

In embodiments, the gellant is a compound of the formula

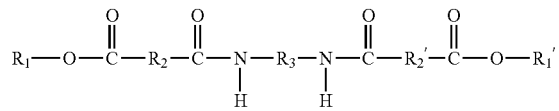

wherein $R_1$ and $R_{1'}$ are the same, and wherein $R_1$ and $R_{1'}$ are each an aromatic group;

wherein $R_2$ and $R_{2'}$ are the same or different, and wherein $R_2$ and $R_{2'}$ are each independently selected from (i) alkylene groups, which can be linear or branched, saturated or unsaturated, cyclic or acyclic, substituted or unsubstituted alkylene groups, and wherein hetero atoms may optionally be present in the alkylene group; (ii) arylene groups, which can be substituted or unsubstituted arylene groups, and wherein hetero atoms may optionally be present in the arylene group; (iii) arylalkylene groups, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) alkylarylene groups, which can be substituted or unsubstituted alkylarylene groups, wherein the alkyl portion of the alkylarylene group can be linear or branched, saturated or unsaturated, cyclic or acyclic, and substituted or unsubstituted, and wherein hetero atoms may optionally be present in either the aryl portion or the alkyl portion of the alkylarylene group; and wherein $R_3$ is (i) a linear or branched alkylene group, which can be saturated or unsaturated, and substituted or unsubstituted alkylene groups, and wherein hetero atoms may optionally be present in the alkylene group; (ii) an arylene group, which can be substituted or unsubstituted arylene groups, and wherein hetero atoms may optionally be present in the arylene group; (iii) an arylalkylene group, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) an alkylarylene group, which can be substituted or unsubstituted alkylarylene groups, wherein the alkyl portion of the alkylarylene group can be linear or branched, saturated or unsaturated, cyclic or acyclic, and substituted or unsubstituted, and where hetero atoms may optionally be present in either the aryl portion or the alkyl portion of the alkylarylene group.

In embodiments, $R_1$ and $R_{1'}$ are selected from the following aromatic groups:

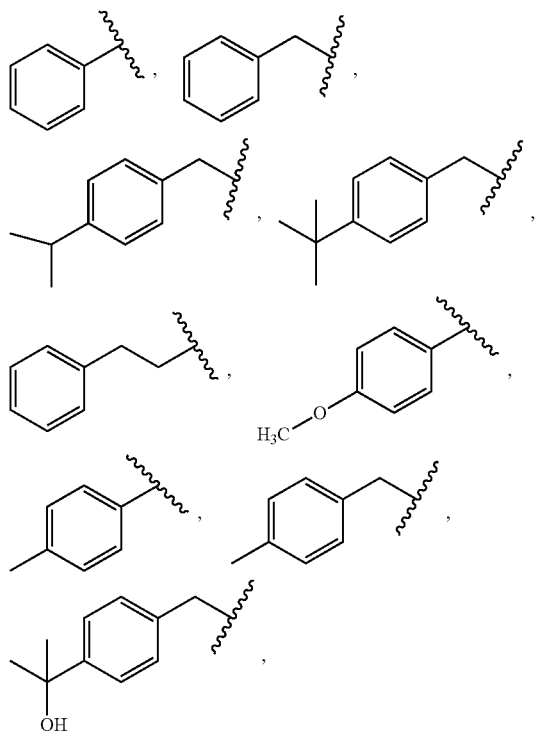

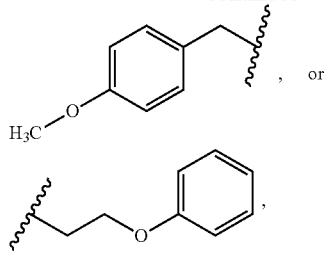

wherein 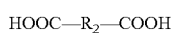 represents the point of attachment of the $R_1$ and $R_{1'}$ group.

The gellant can be prepared by any suitable or desired method. For example, in one specific embodiment, about 2 molar equivalents of a diacid of the formula

HOOC—$R_2$—COOH and about one molar equivalent of a diamine of the formula

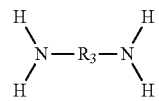

can be reacted by use of a coupling agent such as 1,3-dicylclohexylcarbodimide (DCC) in the present of a catalyst such as 4-dimethylaminopyridine (DMAP) in the presence of a solvent such as methylene chloride ($CH_2Cl_2$) at reduced temperatures followed by eventual warming to about room temperature to produce an organoamide intermediate.

The diacid and the diamine can be present in any desired or effective relative amounts. In embodiments, at least about 1.75 moles of diacid per every 1 mole of diamine, or at least about 2 moles of diacid per every 1 mole of diamine, or no more than about 2.5 moles of diacid per every 1 mole of diamine, or no more than about 2.3 moles of diacid per every 1 mole of diamine, or no more than about 2.1 moles of diacid per every 1 mole of diamine, although the relative amounts can be outside of these ranges.

In one embodiment, to the resulting reaction mixture containing the organoamide intermediate can be added about two molar equivalents of an identical aromatic end cap molecule having the formula

In another embodiment, to the resulting reaction mixture containing the organoamide intermediate can be added about one molar equivalent of a first end cap molecule which is an aromatic alcohol having the formula

as described herein and about one molar equivalent of a second end cap molecule which is an alkyl group having at least one ethylenic unsaturation, an arylalkyl group having at least one ethylenic unsaturation, or an alkylaryl group having at least one ethylenic unsaturation, as described herein. In a specific embodiment, the second end cap molecule is caprolactone acrylate.

The organoamide intermediate and the aromatic alcohol can be present in any desired or effective relative amounts. For example, wherein $R_1$ and $R_{1'}$ are the same and comprise an aromatic alcohol, in one embodiment, at least about 1.75 moles of aromatic alcohol per every 1 mole of organoamide intermediate, or at least about 2 moles of aromatic alcohol per every 1 mole of organoamide intermediate, or at least about 2.25 moles of aromatic alcohol per every 1 mole of organoamide intermediate, or no more than about 3 moles of aromatic alcohol per every 1 mole of organoamide intermediate, or no more than about 2.75 moles of aromatic alcohol per every 1 mole of organoamide intermediate, or no more than about 2.5 moles of aromatic alcohol per every 1 mole of organoamide intermediate, although the relative amounts can be outside of these ranges. In embodiments wherein $R_1$ and $R_{1'}$ are two different species, the combined total amount of $R_1$ and $R_{1'}$ is, in embodiments, at least about 1.75, 2, 2.25 moles per every 1 mole of organoamide intermediate, or no more than about 2.75 or no more than about 2.5 moles (combined total of $R_1$ and $R_{1'}$), although the relative amounts can be outside of these ranges.

The ingredients can be mixed together in the sequence just described and a one pot reaction can be employed. For example, molten organoamide intermediate can be added to a 1 liter round bottomed flask equipped with a magnetic stir bar, followed by dichloromethane solvent with stirring until the organoamide intermediate is completely dissolved to form a clear, golden solution. A catalyst, such as DMAP, can be added, followed by a coupling agent, such as DCC.

Next, in one embodiment, a single species of end cap molecule can be added to the reaction mixture containing the organoamide intermediate.

Alternately, in another embodiment, a first species of end cap molecule being an aromatic alcohol and a second species of end cap molecule that is different from the aromatic alcohol can be added simultaneously to the reaction mixture.

The reaction mixture containing the organoamide intermediate or and the single end cap component or the mixed end cap components can be allowed to stir overnight at room temperature. The reaction contents can then be filtered to remove N,N-dicyclohexylurea (DCHU) by-product. The filtrate can be concentrated on a rotary evaporator resulting in a golden gel-like solid amide gellant. The solid residue can be dried in a vacuum oven, such as for about 2 hours at about 90° C., to remove residual solvent from the amide gellant.

Examples of suitable coupling agents include 1,3-dicyclohexylcarbodiimide (DCC) of the formula

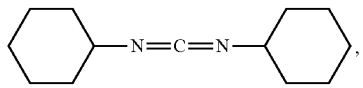

1-(3-(dimethylamino)propyl)3-ethylcarbodiimide HCl (EDCl), N,N-carbonyldiimidazole, N-cyclohexyl-N'-(2-morpholinoethyl)-carbodiimide methyl-p-toluenesulfonate, (benzotriazol-1-yloxy)tris(dimethylamino)phosphonium hexafluorophosphate (BOP), (o-benzotriazol-1-yl)-N,N,N', N'-bis(tetramethylene(uranium hexafluorophosphate (HBTU), bis(2-oxo-3-oxazolidinyl)phosphonic chloride (BOP-Cl), (1H-1,2,3-benzotriazol-1-yloxy)tris(pyrrolidino) phosphonium hexafluoro phosphate (PyBOP), and the like, and mixtures and combinations thereof.

The coupling agent and the diacid can be present in any desired or effective relative amounts. In embodiments, the coupling agent and the diacid are present in an amount of at least about 1.8 moles of coupling agent per every 1 mole of diacid, or at least about 1.9 moles of coupling agent per every 1 mole of diacid, or at least about 2 moles of coupling agent per every 1 mole of diacid, or no more than about 2.75 moles of coupling agent per every 1 mole of diacid, or no more than about 2.5 moles of coupling agent per every 1 mole of diacid, or no more than about 2.2 moles of coupling agent per every 1 mole of diacid, although the relative amounts can be outside of these ranges.

Examples of suitable catalysts include 4-dimethylaminopyridine (DMAP), of the formula

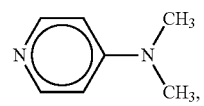

triethylamine, 1,8-diazabicyclo(4a.4.)undec-7-ene (DBU), and the like, and mixtures and combinations thereof.

The catalyst and the diacid are present in any desired or effective relative amounts. In embodiments, the catalyst and the diacid are present in an amount of at least about 0.05 mole of catalyst per every 1 mole of diacid, or at least about 0.1 mole of catalyst per every 1 mole of diacid, or at least about 0.2 mole of catalyst per every 1 mole of diacid, or no more than about 1 mole of catalyst per every 1 mole of diacid, or no more than about 0.8 mole of catalyst per every 1 mole of diacid, or no more than about 0.5 mole of catalyst per every 1 mole of diacid, although the relative amounts can be outside of these ranges.

Any desired or effective solvent can be employed. Examples of suitable solvents include methylene chloride, tetrahydrofuran, methyl ethyl ketone, toluene, dimethyl formamide, diethyl ether, hexane, ethyl acetate, and the like, and mixtures and combinations thereof.

The solvent can be present in any desired or effective amount. In embodiments the solvent can be present in an amount of at least about 10 milliliters of solvent per millimole of diacid, or at least about 15 milliliters of solvent per millimole of diacid, or at least about 20 milliliters of solvent per millimole of diacid, or no more than about 50 milliliters of solvent per millimole of diacid, or no more than about 40 milliliters of solvent per millimole of diacid, or no more than about 30 milliliters of solvent per millimole of diacid, although the amount of solvent can be outside of these ranges.

The reaction between the diacid, the diamine, and the coupling agent can be carried out at any desired or effective temperature, such as from at least about 0° C. to no more than about 50° C., or from about 5° C. to about 40° C., or from about 15° C. to about 30° C., although the temperature can be outside of these ranges.

The subsequent reaction between the resulting amine-terminated diamide intermediate and the additional diacid can be carried out at any desired or effective temperature, such as from at least about 0° C. to no more than about 50° C., or from about 5° C. to about 40° C., or from about 15° C. to about 30° C., although the temperature can be outside of these ranges.

The subsequent reaction between the resulting organoamide intermediate and the aromatic alcohol can be carried out at any desired or effective temperature, such as from at least about 15° C. to no more than about 40° C., or from about 20° C. to about 35° C., or from about 25° C. to about 30° C., although the temperature can be outside of these ranges.

The reaction between the diacid and the diamine can be carried out for any desired or effective period of time, such as for about 2 to about 5 hours, although the period of time can be outside of this range.

The reaction between the organoamide intermediate and the aromatic alcohol, or mixture of aromatic alcohol and second end cap molecule, can be carried out for any desired or effective period of time, such as from about 1.5 hours to about 12 hours, or from about 2 to about 5 hours, or from about 2.5 to about 4 hours, although the period of time can be outside of these ranges.

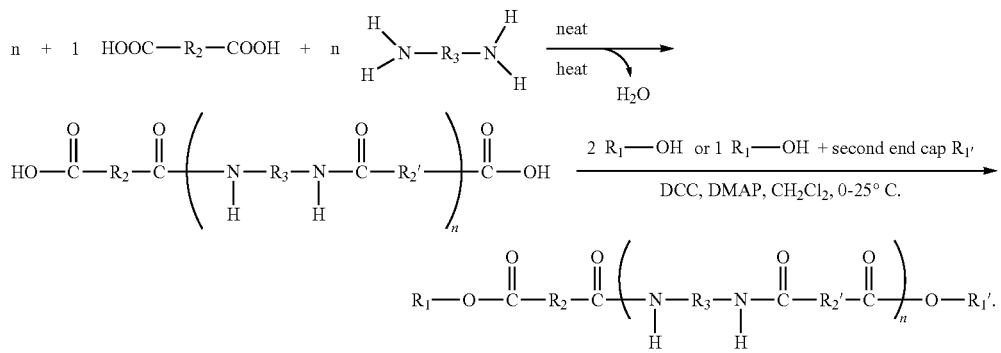

Subsequent to completion of the reaction, the product can be recovered by any desired or effective method, such as filtration of any solid by-products or washing the solution with water depending on the coupling agent used. The solvent can be removed by rotary evaporation. If needed, the product can be purified by washing with acetone and dried in a vacuum oven.

Compounds as disclosed herein can also be prepared by first reacting about n+1 molar equivalents of a diacid of the formula

HOOC—R$_2$—COOH and about n molar equivalent of a diamine of the formula

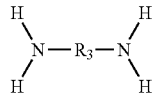

under neat conditions (i.e., in the absence of a solvent) at elevated temperatures while removing water from the reaction mixture to form an acid-terminated organoamide of the formula

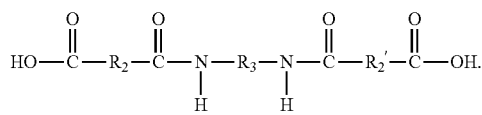

Thereafter, the acid-terminated oligoamide thus formed is reacted with about 2 molar equivalents of an aromatic alcohol of the formula

R$_1$—OH or the acid-terminated organoamide thus formed is reacted with about 1 molar equivalent of an aromatic alcohol of the formula

R$_1$—OH and about 1 molar equivalent of a second end cap molecule which is an alkyl group having at least one ethylenic unsaturation, an arylalkyl group having at least one ethylenic unsaturation, or an alkylaryl group having at least one ethylenic unsaturation, as described herein, by use of a coupling agent such as DCC in the presence of a catalyst such as DMAP in the presence of a solvent such as methylene chloride at reduced temperatures.

The reaction proceeds as follows:

Water can be removed from the reaction mixture between the diacid and the diamine by any desired or effective method, such as by a Dean-Stark trap, molecular sieves, or other dryings agents, or the like.

The reaction between the diacid and the diamine generally is run neat, that is, in the absence of a solvent.

The reaction between the diacid and the diamine can be carried out at any desired effective temperature, such as from about 130° C. to about 180° C., or from about 140° C. to about 175° C., or from about 155° C. to about 165° C., although the temperature can be outside of these ranges.

The reaction between the diacid and the diamine can be carried out for any desired or effective period of time, such as for about 2 to about 5 hours, or from about 2.5 to about 4.5 hours, or from about 3 to about 4 hours, although the period of time can be outside of these ranges.

Thereafter, the acid-terminated organoamide intermediate and the aromatic alcohol (or mixture of aromatic alcohol and second end cap component) are reacted in the presence of a coupling agent and a catalyst.

Suitable coupling agents include those described above, such as DCC. Suitable catalysts include those described above, such as DMAP.

The acid-terminated organoamide intermediate and the aromatic alcohol (or combined total of aromatic alcohol and second end cap component) can be present in any desired or effective relative amounts, in embodiments at least 2 moles of aromatic alcohol per every 1 mole of organoamide intermediate, or no more than about 2.75 moles of aromatic alcohol per every 1 mole of organoamide intermediate, although the relative amounts can be outside of these ranges.

The acid-terminated organoamide intermediate and the coupling agent can be present in any desired or effect relative amounts, in embodiments at least about 1.8 moles of coupling agent per every 1 mole of organoamide intermediate, or no more than about 3 moles of coupling agent per every 1 mole of organoamide intermediate, although the relative amounts can be outside of these ranges.

The catalyst and the organoamide intermediate can be present in any desired or effect relative amounts, in embodiments at least about 0.05 moles of catalyst per every 1 mole of organoamide intermediate, or no more than about 0.8 moles of catalyst per every 1 mole of organoamide intermediate, although the relative amounts can be outside of these ranges.

Any desired or effective solvent can be employed including the solvents described above.

The solvent can be present in any desired or effect relative amounts, in embodiments at least about 20 milliliters of solvent per gram of organoamide intermediate, or no more than about 100 milliliters of solvent per gram of organoamide intermediate, although the amount of solvent can be outside of these ranges.

The reaction between the organoamide intermediate, the aromatic alcohol (or aromatic alcohol and second end cap component), and the coupling agent can be carried out at any desired or effective temperature, such as at least about 15° C. to about 50° C., or from about 20° C. to about 40° C., or from about 25° C. to about 35° C., although the temperature can be outside of these ranges.

The reaction between the acid-terminated organoamide intermediate, the aromatic alcohol (or aromatic alcohol and second end cap component), can be carried out for any desired or effective period of time, such as from about 2 hours to about 12 hours, or from about 2 to about 5 hours, or from about 2.5 to about 4 hours, although the period of time can be outside of these ranges.

Subsequent to completion of the reaction, the product can be recovered by any desired or effective method, such as filtration of any solid by-products or washing the solution with water depending on the coupling agent used. The solvent can be removed by rotary evaporation. If needed, the product can be purified by washing with acetone and dried in a vacuum oven.

In embodiments, the gellant can be selected from those described in U.S. Pat. No. 8,882,256, which is hereby incorporated by reference herein in its entirety. In embodiments, the gellant is a low molecular weight gellant having a weight average molecular weight of from about 800 to about 2,500.

In embodiments, the gellant is a compound of the formula

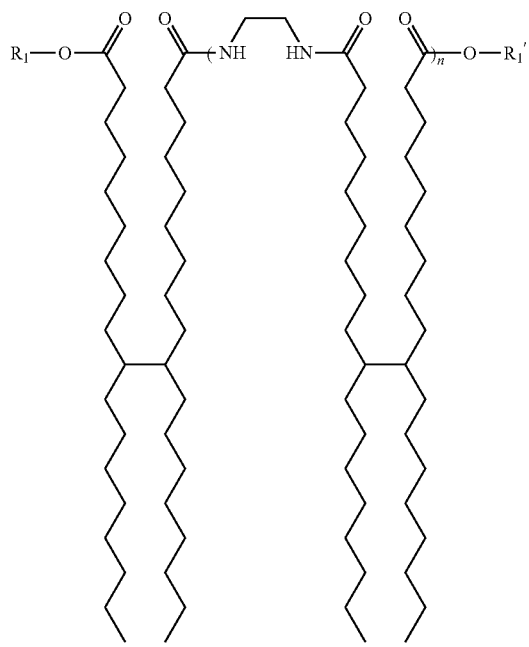

wherein n is 1 to 10, and wherein $R_1$ and $R_{1'}$ each, independently of the other, are aromatic groups selected from the group consisting of:

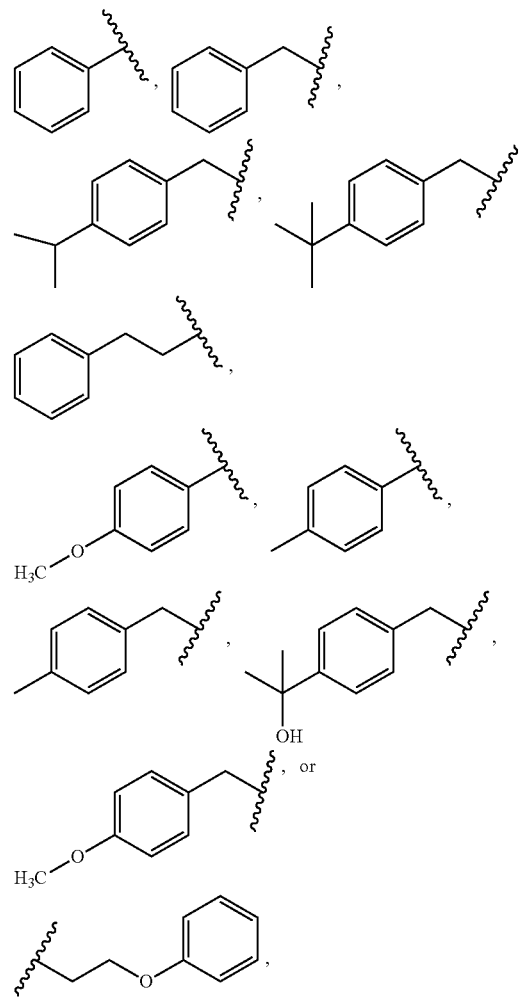

wherein ∿ represents the point of attachment of the $R_1$ and $R_{1'}$ group to the compound.

In embodiments, the gellant has a weight average molecular weight (Mw) of from about 800 to about 2,500, or from about 900 to about 2,400, or from about 1,000 to about 2,300. In embodiments, the amide gellant has a number average molecular weight (Mn) of from about 500 to about 2,400, or from about 700 to about 2,300, or from about 900 to about 1,700.

The gellant of this embodiment can be prepared by any suitable or desired method. In embodiments, the gellant is prepared as described in U.S. Pat. No. 8,882,256, describing a two step process. In the first step, an amide gellant precursor (organoamide) is synthesized by using two equivalents of Pripol® C36 dimer diacid, available from Cognis Corporation, and one equivalent of ethylenediamine (EDA). In the second step, the organoamide is end-capped with various end cap alcohols to make the esters. During the preparation of the organoamide, oligomers or x-mers of the ester-terminated polyamide gellant are created (end-capping to make the esters in the final gellant does not change the oligomer distribution).

By controlling the amount of EDA used in the first step, for example, reducing the amount of EDA used relative to the amount of Pripol®, the distribution can be shifted to create larger proportions of lower order x-mers (smaller values of repeat units n). Typically, the amount of EDA relative to the amount of Pripol® is expressed as an EDA:Pripol® ratio. In embodiments, the EDA:Pripol® ratio used in synthesizing the amide gellant precursor is modified by reducing from the original EDA:Pripol® ratio of 1.1:2 down to from about 0.9:2 to about 0.05:2, or to from about 0.8:2 to about 0.10:2, or to from about 0.75:2 to about 0.25:2.

The gellants can be dissolved in solutions including in curable monomers such as, for example, propoxylated neopentyl glycol diacrylate, such as SR9003®, commercially available from Sartomer Co. Inc.

The gellant is provided in the ink composition in an amount selected to impart a viscosity of less than $10^6$ centipoise, or less than $10^5$ centipoise, or from about $10^2$ centipoise to about $10^4$ centipoise, or from about $10^{2.5}$ centipoise to about $10^{3.5}$ centipoise, at a temperature of from about 20° C. to about 40° C. In embodiments, the gellant is provided in an amount selected to impart a viscosity of from about $10^2$ centipoise to about $10^4$ centipoise, or from about $10^{2.5}$ centipoise to about $10^{3.5}$, at a temperature of from about 25° C. to about 35° C. In embodiments, the gellant is provided in the ink composition in an amount of less than about 5 percent, or less than 5 percent, by weight, based on the total weight of the ink composition. In embodiments, the gellant is provided in the ink composition in an amount of from about 1.5 percent to about 4.5 percent, by weight, based upon the total weight of the ink composition.

In certain embodiments, the gellant comprises an amide gellant present in an amount of from about 1.5 percent to about 4.5 percent, by weight, based upon the total weight of the ink composition.

In certain embodiments, the gellant comprises a low molecular weight amide gellant having a weight average molecular weight of from about 800 to about 2,500; and wherein the low molecular weight amide gellant is present in an amount of from about 1.5 percent to about 4.5 percent, by weight, based upon the total weight of the ink composition.

In certain embodiments, the gellant comprises a bis-urea gellant present in an amount of about 5 percent, by weight, based upon the total weight of the ink composition.

In embodiments the ink composition has the characteristic of being both ink jettable and pinnable at a temperature of from about 25° C. to about 35° C.

In embodiments, the compounds disclosed herein are curable. "Curable" as used herein means polymerizable or chain extendable, that is, a material that can be cured via polymerization, including, but not limited to, free radical polymerization or chain extension, cationic polymerization or chain extension, and/or in which polymerization is photoinitiated through use of a radiation sensitive photoinitiator. Radiation curable as used herein is intended to cover all forms of curing upon exposure to a radiation source, including, but not limited to, light and heat sources and including in the presence or absence of initiators. Examples of radiation curing include, but are not limited to, ultraviolet (UV) light, for example having a wavelength of from about 200 to about 400 nanometers, visible light, or the like, optionally in the presence of photoinitiators and/or sensitizers, electron-beam radiation, optionally in the presence photoinitiators, thermal curing, optionally in the presence of high temperature thermal initiators (and which are in selected embodiments largely inactive at the jetting temperature when used in phase change inks), and appropriate combinations thereof.

The ink vehicle or carrier contains at least one radically curable monomer compound. Examples of suitable monomer compounds include, but are not limited to, propoxylated neopentyl diacrylate, such as SR9003®, commercially available from Sartomer Co. Inc., isobornyl acrylate, isobornyl methacrylate, lauryl acrylate, lauryl methacrylate, isodecylacrylate, isodecylmethacrylate, caprolactone acrylate, 2-phenoxyethyl acrylate, isooctylacrylate, isooctylmethacrylate, butyl acrylate, and the like, as well as mixtures and combinations thereof. In addition, multifunctional acrylate and methacrylate monomers and oligomers can be included in the phase change ink carrier as reactive diluents and as materials that can increase the crosslink density of the cured image, thereby enhancing the toughness of the cured images. Examples of suitable multifunctional acrylate and methacrylate monomers and oligomers include, but are not limited to, pentaerythritol tetraacrylate, pentaerythritol tetramethacrylate, 1,2-ethylene glycol diacrylate, 1,2-ethylene glycol dimethacrylate, 1,6-hexanediol diacrylate, 1,6-hexanediol dimethacrylate, 1,12-dodecanol diacrylate, 1,12-dodecanol dimethacrylate, tris(2-hydroxy ethyl)isocyanurate triacrylate, hexanediol diacrylate, tripropylene glycol diacrylate, dipropylene glycol diacrylate, amine modified polyether acrylates (available as PO 83 F®, LR 8869®, and LR8889®, from BASF Corporation), trimethylolpropane triacrylate, glycerol propoxylate triacrylate, dipentaerythritol pentaacrylate, dipentaerythritol hexaacrylate, ethoxylated pentaerythritol tetraacrylate (available from Sartomer Co. In. as SR494®), and the like, as well as mixtures and combinations thereof.

When a reactive diluent is added to the ink carrier material, the reactive diluent is added in any desired or effective amount, such as from about 1 to about 80 percent by weight of the carrier, or from about 35 to about 70 percent by weight of the carrier, although the amount of diluent can be outside of theses ranges.

The ink carrier is present in the phase change ink in any desired or effective amount, such as from about 0.1 to about 97 percent by weight of the ink, or from about 50 to about 90 percent by weight of the ink, or from about 70 to about 85 percent by weight of the ink, although the amount can be outside of theses ranges.

The ink compositions can further contain an initiator. Examples of free radical initiators include benzyl ketones, monomeric hydroxyl ketones, polymeric hydroxyl ketones, α-amino ketones, acyl phosphine oxides, metallocenes, benzophenone, benzophenone derivatives, and the like. Specific examples include 1-hydroxy-cyclohexylphenylketone, (available as Irgacure® 184 from BASF Corporation), 2-benzyl-2-(dimethylamino)-1-(4-(4-morpholinyl)phenyl)-1-butanone, 2-methyl-1-(4-methylthio)phenyl-2-(4-morpholinyl)-1-propanone, 2,4,6-trimethylbenzoyidiphenylphosphine oxide (available as LUCIRIN TPO® from BASF Corporation), benzyl-dimethylketal, and the like, as well as mixtures and combinations thereof. Further specific examples include isopropylthioxanthone (available as DAROCURE® ITX from BASF Corporation), 2,4,6-trimethylbenzoylethoxyphenylphosphine oxide (available as LUCIRIN TPO-L® from BASF Corporation), bis(2,4,6-trimethylbenzoyl)-phenyl-phosphine oxide (available as IRGACURE® 819 from BASF Corporation Specialty Chemicals), and other acyl phosphines, 2-methyl-1-(4-methylthio)phenyl-2-(4-morpholinyl)-1-proponone (available as IRGACURE® 907 from BASF Corporation Specialty Chemicals), and 1-(4-(2-hydroxyethoxy)phenyl)-2-hydroxy-2-methylpropan-1-one (available as IRGACURE® 2959 from BASF Corporation Specialty Chemicals), 2-benzyl-2-dimethylamino-1-(4-morpholinophenyl)butanone-1 (available as IRGACURE® 369 from BASF Corporation Specialty Chemicals), 2-hydroxy-1-(4-(4-(2-hydroxy-2-methylpropionyl)-benzyl)-phenyl)-2-methylpropan-1-one (available as IRGACURE® 127 from BASF Corporation Specialty Chemicals), 2-dimethylamino-2-(4-methylbenzyl)-1-(4-morpholin-4-ylphenyl)-butanone (available as IRGACURE® 379 from BASF Corporation Specialty Chemicals), titanocenes, 1-hydroxy-cyclohexylphenylketone, 2,4,6-trimethylbenzophenone, 4-methylbenzophenone, 2,4,6-trimethylbenzoylphenylphosphinic acid ethyl ester, oligo(2-hydroxy-2-methyl-1-(4-(1-methylvinyl)phenyl)propanone), 2-hydroxy-2-methyl-1-phenyl-1-propanone, and the like, as well as mixtures and combinations thereof.

Optionally, the inks can also contain an amine synergist, which are co-initiators which can donate a hydrogen atom to a photoinitiator and thereby form a radical species that initiates polymerization, and can also consume dissolved oxygen, which inhibits free-radical polymerization, thereby increasing the speed of polymerization. Examples of suitable amine synergists include, but are not limited to, ethyl-4-dimethylaminobenzoate, 2-ethylhexyl-4-dimethylaminobenzoate, and the like, as well as mixtures and combinations thereof.

Initiators for the inks disclosed herein can absorb radiation at any desired or effective wavelength, in embodiments, from about 200 to about 560 nanometers, or from about 200 to about 420 nanometers, although the wavelength can be outside of these ranges.

The initiator can be present in the ink in any desired or effective amount, in embodiments from about 0.5 to about 15 percent by weight of the ink, or from about 1 to about 10 percent by weight of the ink, although the amount can be outside of these ranges.

The inks can also optionally contain an antioxidant. The optional antioxidants can protect printed images from oxidation and can also protect the ink components from oxidation during the heating portion of the ink preparation process. Specific examples of suitable antioxidant stabilizers include, but are not limited to, NAUGARD®524, NAUGARD®524, NAUGARD®635, NAUGARD® 1-403, and NAUGARD®959, commercially available from Crompton Corporation, IRGANOX® 1010 and IRGASTAB® UV 10, commercially available from BASF Corporation, GENORAD® 16 and GENORAD® 40, commercially available from Rahn AG, and the like, as well as mixtures and combinations thereof.

When present, the optional antioxidant is present in the ink in any desired or effective amount, in embodiments from about 0.01 to about 20 percent by weight of the ink carrier, or from about 0.1 to about 5 percent by weight of the ink carrier, or from about 1 to about 3 percent by weight of the ink carrier, although the amount can be outside of these ranges.

The inks can also contain a colorant. Any desired or effective colorant can be employed, including dyes, pigments, mixtures thereof, and the like, provided that the colorant can be dissolved or dispersed in the ink vehicle. Examples of suitable dyes include, but are not limited to, Usharect Blue 86 (Direct Blue 86), available from Ushanti Colour; Intralite Turquoise 8GL (Direct Blue 86), available from Classic Dyestuffs; Chemictive Brilliant Red 7BH (Reactive Red 4), available from Chemiequip; Levafix Black EB, available from Bayer; Reactron Red H8B (Reactive Red 31), available from Atlas Dye-Chem; D&C Red #28 (Acid Red 92), available from Warner-Jenkinson; Direct Brilliant Pink B, available from Global Colors; Acid Tartrazine, available from Metrochem Industries; Cartasol Yellow 6GF, available from Clariant; Carta Blue 2GL, available from Clariant; solvent dyes, including spirit soluble dyes such as Neozapon Red 492 (BASF); Orasol Red G (BASF Corporation); Direct Brilliant Pink B (Global Colors); Aizen Spilon Red C-BH (Hodogaya Chemical); Kayanol Red 3BL (Nippon Kayaku); Spirit Fast Yellow 3G; Aizen Spilon Yellow C-GNH (Hodogaya Chemical); Cartasol Brilliant Yellow 4GF (Clariant); Pergasol Yellow CGP (BASF Corporation); Orasol Black RLP (BASF Corporation); Savinyl Black RLS (Clariant); Morfast Black Conc. A (Rohm and Haas); Orasol Blue GN (BASF Corporation); Savinyl Blue GLS (Sandoz); Luxol Fast Blue MBSN (Pylam); Sevron Blue SGMF (Classic Dyestuffs); Basacid Blue 750 (BASF); Neozapon Black X51 [C.I. Solvent Black, C.I. 12195] (BASF); Sudan Blue 670 [C.I. 61554] (BASF); Sudan Yellow 146 [C.I. 12700] (BASF); Sudan Red 462 [C.I. 260501] (BASF); and the like, as well as mixtures thereof.

Pigments are also suitable colorants for the inks. Examples of suitable pigments include PALIOGEN® Violet 5100 (BASF); PALIOGEN® Violet 5890 (BASF); HELIOGEN® Green L8730 (BASF); LITHOL® Scarlet D3700 (BASF); SUNFAST® Blue 15:4 (Sun Chemical); Hostaperm® Blue B2G-D (Clariant); Permanent Red P-F7RK; Hostaperm® Violet BL (Clariant); LITHOL® Scarlet 4440 (BASF); Bon Red® C (Dominion Color Company); ORACET® Pink RF (BASF Corporation); PALIOGEN® Red 3871 K (BASF); SUNFAST® Blue 15:3 (Sun Chemical); PALIOGEN® Red 3340 (BASF); SUNFAST® Carbazole Violet 23 (Sun Chemical); LITHOL® Fast Scarlet L4300 (BASF); SUNBRITE® Yellow 17 (Sun Chemical); HELIOGEN® Blue L6900, L7020 (BASF); SUNBRITE® Yellow 74 (Sun Chemical); SPECTRA PAC® C Orange 16 (Sun Chemical); HELIOGEN® Blue K6902, K6910 (BASF); SUNFAST® Magenta 122 (Sun Chemical); HELIOGEN® Blue D6840, D7080 (BASF); Sudan Blue OS (BASF); NEOPEN® Blue FF4012 (BASF); PV Fast Blue B2GO1 (Clariant); IRGALITE® Blue BCA (BASF Corporation); PALIOGEN® Blue 6470 (BASF); Sudan Orange G (Aldrich), Sudan Orange 220 (BASF); PALIOGEN® Orange 3040 (BASF); PALIOGEN® Yellow 152, 1560 (BASF); LITHOL® Fast Yellow 0991 K (BASF); PALIOTOL® Yellow 1840 (BASF); NOVOPERM® Yellow FGL (Clariant); Lumogen® Yellow D0790 (BASF); Suco-Yellow L1250 (BASF); Suco-Yellow D1355 (BASF); Suco Fast Yellow D1 355, D1 351 (BASF); HOSTAPERM® Pink E 02 (Clariant); Hansa Brilliant Yellow 5GX03 (Clariant); Permanent Yellow GRL 02 (Clariant); Permanent Rubine L6B 05 (Clariant); FANAL Pink D4830 (BASF); CINQUASIA® Magenta (DU PONT); PALIOGEN® Black L0084 (BASF); Pigment Black K801 (BASF); and carbon blacks such as REGAL 330™ (Cabot), Carbon Black 5250, Carbon Black 5750 (Columbia Chemical), and the like, as well as mixtures thereof.

In another specific embodiment, the colorant is a curable olefin colorant such as those disclosed in U.S. Pat. Nos. 6,870,063, 6,870,062, 6,787,658, and 7,141,685, the disclosures of each of which are totally incorporated herein by reference.

The colorant is present in any desired or effective amount to obtain the desired color or hue, in embodiments from about 0.1 percent to about 15 percent by weight of the ink, or from about 0.2 percent to about 8 percent by weight of the ink, although the amount can be outside of these ranges.

The inks can also, if desired, contain additives to take advantage of the known functionality associated with such additives. Such additives may include, for example, defoamers, slip and leveling agents, pigment dispersants, and the like, as well as mixtures and combinations thereof. The inks can also include additional monomeric or polymeric materials as desired.

Curing of the ink can be effected by exposure of the ink image to actinic radiation at any desired or effective wavelength, in embodiments from about 200 nanometers to about 480 nanometers, although the wavelength can be outside of this range. Exposure to actinic radiation can be for any desired or effective period of time, in embodiments for about 0.2 second to about 30 seconds, or from about 1 second to 15 seconds, although the exposure period can be outside of these ranges. By curing is meant that the curable compounds in the ink undergo an increase in molecular weight upon exposure to actinic radiation, such as (but not limited to) crosslinking, chain lengthening, or the like.

The ink compositions can be prepared by any desired or suitable method. For example, the ink ingredients can be mixed together, followed by heating, to a temperature of, in embodiments, at least about 80° C. or no more than about 120° C., although the temperature can be outside of this ranges, and stirring until a homogeneous ink composition is obtained, followed by cooling the ink to ambient temperature (typically from about 20 to about 25° C.).

The inks can be employed in apparatus for direct printing ink jet processes and in indirect (offset) printing ink jet applications. Another embodiment disclosed herein is directed to a process which comprises incorporating an ink as disclosed herein into an ink jet printing apparatus, melting the ink, and causing droplets of the melted ink to be ejected in an imagewise pattern onto a recording substrate. A direct printing process is also disclosed in, for example, U.S. Pat. No. 5,195,430, the disclosure of which is totally incorporated herein by reference. Yet another embodiment disclosed herein is directed to a process which comprises incorporating an ink as disclosed herein into an ink jet printing apparatus, melting the ink, causing droplets of the melted ink to be ejected in an imagewise pattern onto an intermediate transfer member, and transferring the ink in the imagewise pattern from the intermediate transfer member to a final recording substrate. In a specific embodiment, the intermediate transfer member is heated to a temperature above that of the final recording sheet and below that of the melted ink in the printing apparatus. An offset or indirect printing process is also disclosed in, for example, U.S. Pat. No. 5,389,958, the disclosure of which is totally incorporated herein by reference. In one specific embodiment, the printing apparatus employs a piezoelectric printing process wherein droplets of the ink are caused to be ejected in imagewise pattern by oscillations of piezoelectric vibrating elements. Inks as disclosed herein can also be employed in other hot melt printing processes, such as hot melt acoustic ink jet printing, hot melt thermal ink jet printing, hot melt continuous stream or deflection ink jet printing, and the like. Phase change inks as disclosed herein can also be used in printing processes other than hot melt ink jet printing processes. In embodiments, the process comprises exposing the imagewise pattern to ultraviolet radiation.

In embodiments, a method for printing comprises disposing an ink composition as described herein in an imagewise pattern onto an intermediate transfer member or directly onto a final image receiving substrate; optionally, when an intermediate transfer member is used, transferring the ink in the imagewise pattern from the intermediate transfer member to a final recording substrate; exposing the imagewise pattern to radiation to cure the ink; wherein the ink composition comprises at least one curable monomer; at least one gellant; an optional photoinitiator; and an optional colorant; wherein the ink composition has a viscosity of less than $10^6$ centipoise at a temperature of from about 20° C. to about 40° C.; and wherein the ink composition has the characteristics of being both ink jettable and pinnable at a temperature of from about 20° C. to about 40° C.

In embodiments, the method further comprises providing a shearing or mechanical assist to the ink composition to enable or assist jetting at a temperature of from about 20 to about 40° C. In embodiments, this shearing can be achieved with a recirculating print head that 'pumps' the ink through the reservoir and print head body to keep the ink moving. Alternatively, one could have a mixing element, such as a blade, within the reservoir.

EXAMPLES

The following Examples are being submitted to further define various species of the present disclosure. These Examples are intended to be illustrative only and are not intended to limit the scope of the present disclosure. Also, parts and percentages are by weight unless otherwise indicated.

The ink compositions herein, having room temperature viscosities of from about $10^2$ to about $10^4$ centipoise, are still pinned in place, retaining the substrate latitude exhibited by higher viscosity designs, which is an unexpected and advantageous feature. This phenomenon is demonstrated with both urea and urethane gellants.

Materials used in the examples include the following.

Gellant #1, a bis-urethane organogelator, prepared as described in Example 1.

Gellant #2, an amide gellant, prepared as described in Example 2.

Unilin® 350 acrylate, a curable acrylate wax derived from Unilin® 350 alcohol available from Baker Petrolite, (C22, C23, C24 mixture, melting point about 50 to about 60 C). Unilin® 350 can be used as received or synthesized as described in U.S. Pat. No. 7,559,639, which is hereby incorporated by reference herein in its entirety.

HDDA, hexanediol diacrylate.

SR9003®, a low viscosity propoxylated (2) neopentyl glycol diacrylate monomer available from Sartomer Company, Inc.

SR238®, a 1,6-hexanediol diacrylate available from Sartomer Company, Inc.

SR399LV®, a low viscosity dipentaerythritol pentaacrylate (pentafunctional acrylate ester) monomer available from Sartomer Company, Inc.

IRGACURE® 379, an α-amino ketone photoinitiator comprising 2-dimethylamino-2-(4-methylbenzyl)-1-(4-morpholin-4-ylphenyl)-butanone, melting range 82 to 87° C., available from BASF Corporation.

IRGACURE® 819, a bis acyl phosphine photoinitiator comprising bis(2,4,6-trimethyl benzoyl)-phenylphosphineoxide, melting point 127 to 133° C., available from BASF Corporation.

Esacure® KIP 150, oligo[2-hydroxy-2-methyl-1-[4-(1-methylvinyl)phenyl]propanone], available from IGM Resins.

IRGASTAB® UV-10, a nitroxyl based stabilizer available from BASF Corporation.

Pigment Dispersion #1, a cyan pigment dispersion containing cyan pigment, EFKA® 4340 dispersant, and SR9003® monomer, prepared as described in Example 3.

Example 1

Synthesis of bis-urea gellant. Into a solution containing Desmodur W (H12MDI, 4.91 grams, 18.70 mmol; obtained from Bayer) and hexane (40 milliliters) with stirring at room temperature was added stearylamine (10.08 grams, 37.4 mmol; obtained from Sigma-Aldrich Fine Chemicals). The resulting solution was heated to reflux for 1 hour after which time the IR spectrum indicated that the isocyanate starting material was consumed. The reaction mixture wax cooled to room temperature during which time a white fluffy precipitate was formed. The produce was filtered on a Buchner funnel and the filter cake was washed with hexanes and dried on a vacuum pump to furnish 15 grams (18.7 mmol, 100% yield) of a white fluffy solid. The bis-urea gellant is believed to be a compound of the formula

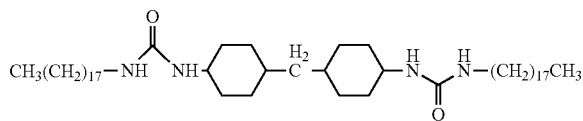

Example 2

Synthesis of amide gellant #2. A phenyl glycol gellant compound was prepared as follows. 64.06 grams of molten organoamide precursor described above (55.3 millimoles, 1 equivalent) were added to a 1 liter round bottomed flask equipped with a magnetic stir bar. Next, 350 milliliters of dichloromethane were added, and the mixture was stirred until all of the organoamide was dissolved. Next, 4,4-dimethylaminopyridine (1.014 grams, 8.30 millimoles, 0.15 equivalent) was added, followed by addition of 1,3-dicyclohexylcarbodiimide (27.4 grams, 133 millimoles, 2.4 equivalents). After 15 minutes, a cloudy suspension formed. To the suspension was added phenyl glycol (15.29 grams, 111 millimoles, 2 equivalents), and the reaction was allowed to stir overnight at room temperature. The next day, the reaction mixture was filtered to remove N,N-dicyclohexylurea (by-product) and the filtrate solvent was removed in vacuo to yield an off-white, opaque solid. The solid residue was dried in a vacuum oven for 2 hours at 90° C. to remove residual solvent, to furnish 41.5 grams (29.7 millimoles, 53.6% yield) of phenyl glycol gellant product as a translucent gel believed to be of the formula

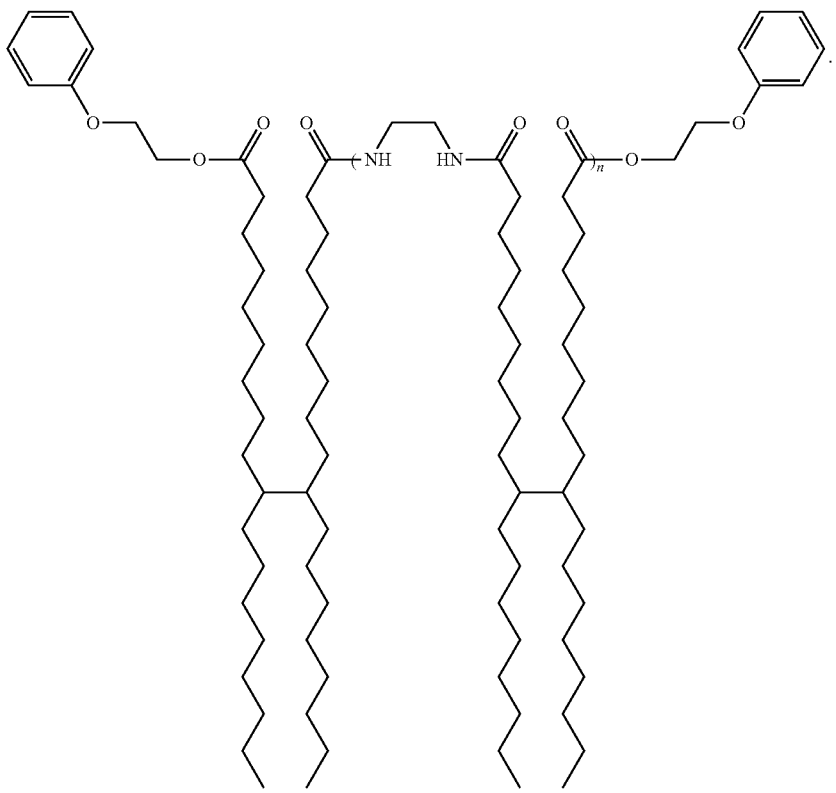

¹H NMR (ppm, CDCl₃, 300 MHz, room temperature): δ 7.31 (4H, m, ArH), 6.94 (6H, m, ArH), 4.44 (4H, J=4.8 Hz, ArOCH2), 4.19 (4H, t, J=5.1 Hz, ArOCH₂CH₂), 3.38 (4H, br, NHCH₂CH₂NH), 2.36 (4H, t, J=7.5 Hz, α-CH2 (ester)), 2.19 (4H, t, J=7.5 Hz, α-CH₂ (amide)), 1.95-0.85 (br, aliphatic H).

Example 3

Preparation of Cyan Pigment Dispersion #1. To a 4 Liter jacketed stainless steel container was added SR9003® (1,166.2 grams) and EFKA® 4340 (993.8 grams of a 32.4 solids in SR9003®). This was stirred using a high speed mixer and to this was added cyan pigment (Sun Spectra Pac®, 540 grams) over 1 hour. The mixer was replaced with a basket mill (Hockmeyer, 0.1 millimeter screen) containing zirconium beads (0.3 millimeter, 40 grams) and the RPM was increased to 5500 over 5 minutes while cooling the jacketed reactor. Upon reaching 5500 RPM, the basket mill was operated for 3 hours while maintaining a reaction temperature of 90° C. The basket mill was raised and the dispersion was discharged to afford a cyan dispersion of 20% solids content.

Example 4

Ink formulation containing 5 weight percent of the bis-urea gelator of Example 1. To a 20 milliliter amber glass vial as added the bis-urea gellator of Example 2, Unilin® 350 acrylate, SR9003® or SR238® monomer, SR399LV®, IRGACURE® 379, IRGACURE® 819, Esacure® KIP 150, and IRGASTAB® UV10 in the amounts as shown in Table 1. The mixture was stirred with a magnetic stir bar and heated to 90° C. for 1 hour to form a clear solution. Finally, the pigment dispersion concentrate of Example 3 was added and the mixture was heated with stirring for an additional hour at 90° C.

TABLE 1

| Component | Weight Percent | m/g |
|---|---|---|
| Gellant #1, Example 1 | 5.00 | 1.0 |
| Unilin ® 350 acrylate (PP-U350Ac-4) | 2.00 | 0.4 |
| HDDA | 70.30 | 14.1 |
| SR399LV ® | 5.00 | 1.0 |
| IRGACURE ® 379 | 3.00 | 0.6 |
| IRGACURE ® 819 | 0.50 | 0.1 |
| Esacure ® KIP 150 | 4.00 | 0.8 |
| IRGASTAB ® UV-10 | 0.20 | 0.04 |
| Pigment Dispersion #1, Example 3 | 10.00 | 2.0 |
| TOTAL | 100 | 20 |

Comparative Example 5

Comparative Ink Example 5. An ink composition having 7.5 weight percent of the amide gellant #2 of Example 2 was prepared as follows. An ink composition was prepared by combining the components in Table 2 below in the amounts listed according to the processes described herein. To a 600 milliliter beaker was added the amide gellant #2 of Example 2 above, Unilin® 350 acrylate, SR9003®, SR399LV®, IRGACURE® 379, DAROCUR® ITX, IRGACURE® 819, IRGACURE® 127, and IRGASTAB® UV-10. The mixture was stirred with a magnetic stir bar and heated to 90° C. for 1 hour to form a clear solution. The solution was hot filtered through a 1 micrometer Parker filter with pressure and transferred to a dropping funnel fitted with heater tape. The filtered base was slowly added to the cyan pigment dispersion in a heated 600 milliliter beaker with stirring over 1 hour. The ink was mixed for 2 hours at 90° C., and filtered again through a 1 micrometer Parker filter with pressure.

TABLE 2

| Component | Weight % | m/g |
|---|---|---|
| Amide gellant #2 of Example 2 | 7.5 | 37.5 |
| Unilin ® 350 Acrylate-prepared as described in U.S. Pat. No. 7,559,639 | 5 | 25 |
| SR9003 ® | 52.8 | 264 |
| SR399LV ® | 5 | 25 |
| IRGACURE ® 379 | 3 | 15 |
| DAROCUR ® ITX | 2 | 10 |
| IRGACURE ® 819 | 1 | 5 |
| IRGACURE ® 127 | 3.5 | 17.5 |
| IRGASTAB ® UV10 | 0.2 | 1 |
| Pigment Dispersion #1, Example 3 | 20 | 100 |
| TOTAL | 100 | 500 |

Example 6

Ink Example 6 was prepared as in Comparative Ink Example 5, except having 4.5 weight percent of the amide gellant #2 of Example 2.

Example 7

Ink Example 7 was prepared as in Comparative Ink Example 5, except having 3 weight percent of the amide gellant #2 of Example 2.

Example 8

Ink Example 8 was prepared as in Comparative Ink Example 5, except having 1.5 weight percent of the amide gellant #2 of Example 2.

Rheology of the ink of Example 4 containing the bis-urea gellant #1 of Example 1 was determined. Temperature dependent complex viscosity of was measured using a controlled-strain rheometer from TA Instruments (RFS-3) at a constant frequency of 1 Hz. Results are shown in FIG. 1. The diurethane gelators can cover a wide scope of viscosity ranges, and can be tuned for optimum phase change temperature and ultimate viscosity at room temperature, which can be advantageous, for example, for non-contact leveling.

Figure 2:
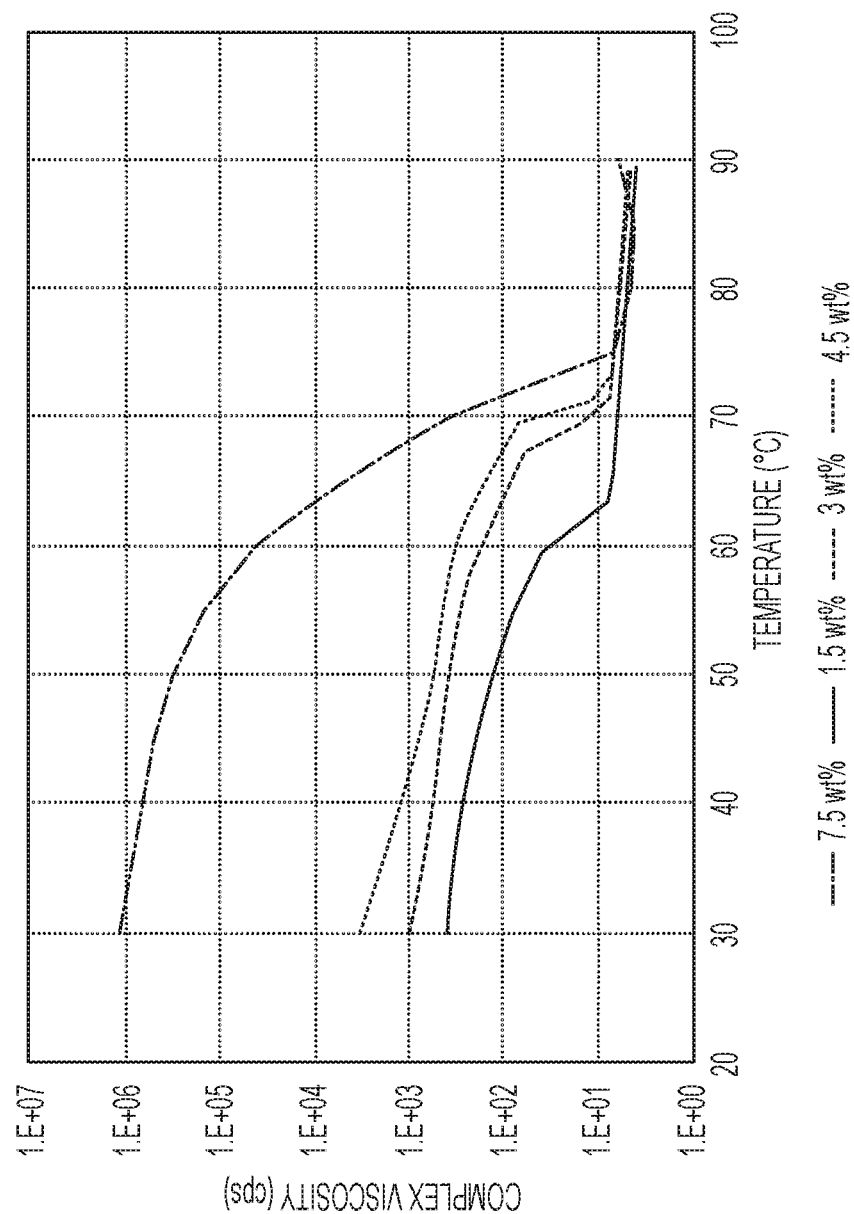
FIG. 2 is a graph showing complex viscosity (y-axis, centipoise) versus temperature (x-axis, ° C.) for a comparative ink and three ink compositions in accordance with the present disclosure.

Ink viscosity as a function of amide gellant concentration for Comparative Example 5 and Examples 6, 7, and 8 were determined. Results are shown in FIG. 2. In Comparative Ink Example 5, the gellant concentration is 7.5 weight percent. By lowering the concentration of the gellant to from 4.5 weight percent to 3 weight percent to 1.5 weight percent (Examples 6, 7, and 8, respectively), the room temperature viscosity of the ink composition drops to within the desired range, in embodiments, to from about $10^2$ to about $10^4$ centipoise.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

The invention claimed is:

1. An ink composition comprising:
   at least one curable monomer;
   at least one gellant;
   an optional photoinitiator; and
   an optional colorant;
   wherein the ink composition has a viscosity of from about $10^2$ centipoise to about $10^4$ centipoise at a temperature of from about 20° C. to about 40° C.; and
   wherein the ink composition has the characteristic of being both ink jettable and pinnable at a temperature of from about 20° C. to about 40° C.

2. The ink composition of claim 1, wherein the ink composition has a viscosity of from about $10^2$ centipoise to about $10^4$ centipoise at a temperature of from about 25° C. to about 35° C.

3. The ink composition of claim 1, wherein the ink composition has a viscosity of from about $10^{2.5}$ centipoise to about $10^{3.5}$ centipoise at a temperature of from about 20° C. to about 40° C.

4. The ink composition of claim 1, wherein the ink composition has a viscosity of from about $10^{2.5}$ centipoise to about $10^{3.5}$ centipoise at a temperature of from about 25° C. to about 35° C.

5. The ink composition of claim 1, wherein the at least one gellant is a gellant selected from the group consisting of amide gellants, bis-urea gellants, and combinations thereof.

6. The ink composition of claim 1, wherein the at least one gellant is a low molecular weight amide gellant having a weight average molecular weight of from about 800 to about 2,500.

7. The ink composition of claim 1, wherein the at least one gellant is a compound of the formula

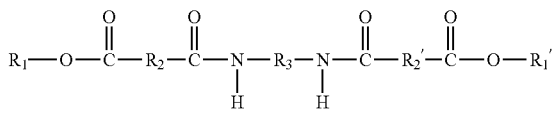

wherein $R_1$ and $R_{1'}$ can be the same or different, and wherein $R_1$ and $R_{1'}$ each, independently of the other is (i) an alkyl group having a least one ethylenic unsaturation therein, which can be linear or branched, cyclic or acyclic, and substituted or unsubstituted alkyl groups, and wherein hetero atoms may optionally be present in the alkyl group, (ii) an arylalkyl group having at least one ethylenic unsaturation therein, which can be substituted or unsubstituted arylalkyl groups, wherein the alkyl portion of arylalkyl group can be linear or branched, cyclic or acyclic, and substituted or unsubstituted, and wherein hetero atoms may optionally be present in either the aryl portion or the alkyl portion of the arylalkyl group, (iii) an alkylaryl group having at least one ethylenic unsaturation therein, which can be substituted or unsubstituted alkylaryl groups, wherein the alkyl portion of the alkylaryl group can be linear or branched, cyclic or acyclic, and substituted or unsubstituted, and wherein hetero atoms may optionally be present in either the aryl or the alkyl portion of the alkylaryl group, or (iv) an aromatic group, provided that at least one of $R_1$ and $R_{1'}$ is an aromatic group; and provided that neither of $R_1$ or $R_{1'}$ is a photoinitiator group;

wherein $R_2$ and $R_{2'}$ are the same or different, and wherein $R_2$ and $R_{2'}$ are each independently selected from (i) alkylene groups, which can be linear or branched, saturated or unsaturated, cyclic or acyclic, substituted or unsubstituted alkylene groups, and wherein hetero atoms may optionally be present in the alkylene group; (ii) arylene groups, which can be substituted or unsubstituted arylene groups, and wherein hetero atoms may optionally be present in the arylene group; (iii) arylalkylene groups, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) alkylarylene groups, which can be substituted or unsubstituted alkylarylene groups, wherein the alkyl portion of the alkylarylene group can be linear or branched, saturated or unsaturated, cyclic or acyclic, and substituted or unsubstituted, and wherein hetero atoms may optionally be present in either the aryl portion or the alkyl portion of the alkylarylene group; and wherein $R_3$ is (i) a linear or branched alkylene group, which can be saturated or unsaturated, and substituted or unsubstituted alkylene groups, and wherein hetero atoms may optionally be present in the alkylene group; (ii) an arylene group, which can be substituted or unsubstituted arylene groups, and wherein hetero atoms may optionally be present in the arylene group; (iii) an arylalkylene group, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) an alkylarylene group, which can be substituted or unsubstituted alkylarylene groups, wherein the alkyl portion of the alkylarylene group can be linear or branched, saturated or unsaturated, cyclic or acyclic, and substituted or unsubstituted, and where hetero atoms may optionally be present in either the aryl portion or the alkyl portion of the alkylarylene group.

8. The ink composition of claim 1, wherein the at least one gellant is a compound of the formula

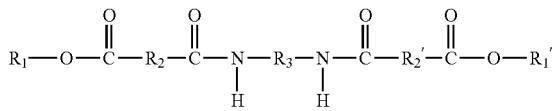

wherein $R_1$ and $R_{1'}$ are the same, and wherein $R_1$ and $R_{1'}$ are each an aromatic group;

wherein $R_2$ and $R_{2'}$ are the same or different, and wherein $R_2$ and $R_{2'}$ are each independently selected from (i) alkylene groups, which can be linear or branched, saturated or unsaturated, cyclic or acyclic, substituted or unsubstituted alkylene groups, and wherein hetero atoms may optionally be present in the alkylene group; (ii) arylene groups, which can be substituted or unsubstituted arylene groups, and wherein hetero atoms may optionally be present in the arylene group; (iii) arylalkylene groups, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) alkylarylene groups, which can be substituted or unsubstituted alkylarylene groups, wherein the alkyl portion of the alkylarylene group can be linear or branched, saturated or unsaturated, cyclic or acyclic, and substituted or unsubstituted, and wherein hetero atoms may optionally be present in either the aryl portion or the alkyl portion of the alkylarylene group; and wherein $R_3$ is (i) a linear or branched alkylene group, which can be saturated or unsaturated, and substituted or unsubstituted alkylene groups, and wherein hetero atoms may optionally be present in the alkylene group; (ii) an arylene group, which can be substituted or unsubstituted arylene groups, and wherein hetero atoms may optionally be present in the arylene group; (iii) an arylalkylene group, which can be substituted or unsubstituted arylalkylene groups, wherein the alkyl portion of the arylalkylene group can be linear or branched, saturated or unsaturated, cyclic or acyclic, and substituted or unsubstituted, and wherein hetero atoms may optionally be present in either the aryl portion or the alkyl portion of the arylalkylene group; or (iv) an alkylarylene group, which can be substituted or unsubstituted alkylarylene groups, wherein the alkyl portion of the alkylarylene group can be linear or branched, saturated or unsaturated, cyclic or acyclic, and substituted or unsubstituted, and where hetero atoms may optionally be present in either the aryl portion or the alkyl portion of the alkylarylene group.

9. The ink composition of claim 1, wherein the at least one gellant is a compound of the formula

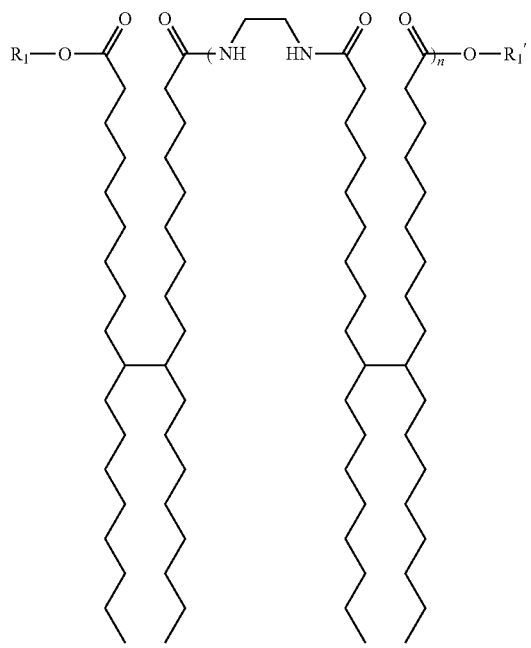

wherein n is 1 to 10, and wherein $R_1$ and $R_1'$ each, independently of the other, are aromatic groups selected from the group consisting of:

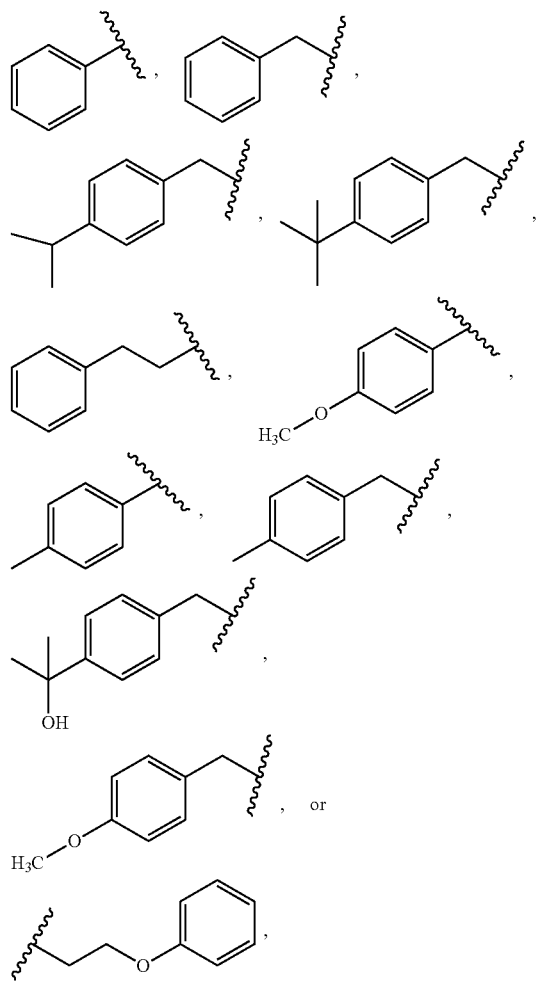

wherein ～ represents the point of attachment of the $R_1$ and $R_1'$ group to the compound.

10. The ink composition of claim 1, wherein the gellant comprises an amide gellant present in an amount of from about 1.5 percent to about 4.5 percent, by weight, based upon the total weight of the ink composition.

11. The ink composition of claim 1, wherein the gellant comprises a low molecular weight amide gellant having a weight average molecular weight of from about 800 to about 2,500; and wherein the low molecular weight amide gellant is present in an amount of from about 1.5 percent to about 4.5 percent, by weight, based upon the total weight of the ink composition.

12. The ink composition of claim 1, wherein the gellant comprises a bis-urea gellant present in an amount of about 5 percent, by weight, based upon the total weight of the ink composition.

13. The ink composition of claim 1, wherein the ink composition has the characteristics of being both ink jettable and pinnable at a temperature of from about 25° C. to about 35° C.

14. A method for printing comprising:
disposing an ink composition in an imagewise pattern onto an intermediate transfer member or directly onto a final image receiving substrate;
optionally, when an intermediate transfer member is used, transferring the ink in the imagewise pattern from the intermediate transfer member to a final recording substrate;

exposing the imagewise pattern to radiation to cure the ink;

wherein the ink composition comprises at least one curable monomer; at least one gellant; an optional photoinitiator; and an optional colorant; wherein the ink composition has a viscosity of from about $10^2$ centipoise to about $10^4$ centipoise at a temperature of from about 20° C. to about 40° C.; and wherein the ink composition has the characteristic of being both ink jettable and pinnable at a temperature of from about 20° C. to about 40° C.

15. The method of claim 14, wherein the gellant comprises an amide gellant present in an amount of from about 1.5 percent to about 4.5 percent, by weight, based upon the total weight of the ink composition.

16. The method of claim 14, wherein the gellant comprises a bis-urea gellant present in an amount of about 5 percent, by weight, based upon the total weight of the ink composition.

17. The method of claim 14, wherein the ink composition has a viscosity of from about $10^2$ centipoise to about $10^4$ centipoise at a temperature of from about 25° C. to about 35° C.

18. The method of claim 14, further comprising:

providing a shearing or mechanical assist to the ink composition to enable jetting at a temperature of from about 20 to about 40° C.

* * * * *